United States Patent
Fujii et al.

(10) Patent No.: US 10,864,004 B2
(45) Date of Patent: Dec. 15, 2020

(54) FLEXIBLE-MANIPULATOR SHEATH AND MANIPULATOR

(71) Applicant: OLYMPUS CORPORATION, Tokyo (JP)

(72) Inventors: Yuta Fujii, Tokyo (JP); Toshihiro Yoshii, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 204 days.

(21) Appl. No.: 16/166,348

(22) Filed: Oct. 22, 2018

(65) Prior Publication Data

US 2019/0054639 A1    Feb. 21, 2019

Related U.S. Application Data

(63) Continuation of application No. PCT/JP2016/063433, filed on Apr. 28, 2016.

(51) Int. Cl.
  *A61B 17/29* (2006.01)
  *A61B 17/22* (2006.01)
  *A61B 17/28* (2006.01)

(52) U.S. Cl.
  CPC ........ *A61B 17/29* (2013.01); *A61B 17/22031* (2013.01); *A61B 17/28* (2013.01); *A61B 2017/2905* (2013.01)

(58) Field of Classification Search
  CPC ... A61B 17/22031; A61B 17/28; A61B 17/29; A61B 2017/22034; A61B 2017/22035; A61B 2017/2901; A61B 2017/2902; A61B 2017/2905
  See application file for complete search history.

(56) References Cited

U.S. PATENT DOCUMENTS

| | | |
|---|---|---|
| 5,286,154 A | 2/1994 | Jens et al. |
| 2004/0019352 A1 | 1/2004 | Kidooka |
| 2004/0092794 A1 | 5/2004 | Chin et al. |
| 2006/0252993 A1 | 11/2006 | Freed et al. |
| 2012/0067604 A1 | 3/2012 | Isobe et al. |

(Continued)

FOREIGN PATENT DOCUMENTS

| | | |
|---|---|---|
| EP | 0501648 A2 | 9/1992 |
| EP | 2508120 A1 | 10/2012 |
| JP | S56-045682 U | 4/1981 |

(Continued)

OTHER PUBLICATIONS

Japanese Office Action dated Jun. 11, 2019 in Japanese Patent Application No. 2018-514068.

(Continued)

*Primary Examiner* — Melanie R Tyson
(74) *Attorney, Agent, or Firm* — Scully, Scott, Murphy & Presser, P.C.

(57) ABSTRACT

Provided is a flexible-manipulator sheath including: a flexible inner tube having a lumen along a longitudinal direction thereof, the lumen configured to insert a wire; a flexible outer tube disposed to cover an outer circumferential surface of the inner tube, the outer tube having a higher compression stiffness than the inner tube; and a cushioning disposed at a space between an inner surface of the outer tube and an outer surface of the inner tube, wherein the cushioning is formed by at least one of filling the space with a viscous material and disposing an elastic sheet at the space.

15 Claims, 6 Drawing Sheets

(56) References Cited

U.S. PATENT DOCUMENTS

2012/0116253 A1  5/2012  Wallace et al.

FOREIGN PATENT DOCUMENTS

| | | |
|---|---|---|
| JP | S63-115532 A | 5/1988 |
| JP | H07-181136 A | 7/1995 |
| JP | H10-276965 A | 10/1998 |
| JP | 2004-057454 A | 2/2004 |
| JP | 2004-268605 A | 9/2004 |
| JP | 2005-176941 A | 7/2005 |
| JP | 2005-296304 A | 10/2005 |
| JP | 2006-505348 A | 2/2006 |
| JP | 2009-022623 A | 2/2009 |
| JP | 2009-530051 A | 8/2009 |
| JP | 4420593 B2 | 2/2010 |
| JP | 2010-273924 A | 12/2010 |
| JP | 2013-123508 A | 6/2013 |
| JP | 2015-231496 A | 12/2015 |
| WO | WO 2004/043242 A1 | 5/2004 |
| WO | WO 2007/112185 A2 | 10/2007 |

OTHER PUBLICATIONS

International Search Report dated Jun. 14, 2016 issued in PCT/JP2016/063433.

FLEXIBLE-MANIPULATOR SHEATH AND MANIPULATOR

CROSS-REFERENCE TO RELATED APPLICATIONS

This is a continuation of International Application PCT/JP2016/063433, with an international filing date of Apr. 28, 2016, which is hereby incorporated by reference herein in its entirety.

TECHNICAL FIELD

The present invention relates to a flexible-manipulator sheath and a manipulator.

BACKGROUND ART

A flexible manipulator is equipped with a flexible insertion unit to be inserted into a bending body cavity, and a movable unit disposed at the distal end of the insertion unit, and a sheath is used in the insertion unit. An example of a known sheath in the related art is a resin multi-lumen tube formed of a long flexible member having a plurality of lumens penetrating therethrough in the longitudinal direction (for example, refer to PTL 1).

A wire for driving the movable unit disposed at the distal end of the insertion unit is passed through the lumens in the multi-lumen tube.

CITATION LIST

Patent Literature

{PTL 1} The Publication of Japanese Patent No. 4420593

SUMMARY OF INVENTION

One aspect of the present invention is directed to a flexible-manipulator sheath including: a flexible inner tube having a lumen along a longitudinal direction thereof, the lumen configured to insert a wire; a flexible outer tube disposed to cover an outer circumferential surface of the inner tube, the outer tube having a higher compression stiffness than the inner tube; and a cushioning disposed at a space between an inner surface of the outer tube and an outer surface of the inner tube, wherein the cushioning is formed by at least one of filling the space with a viscous material and disposing an elastic sheet at the space.

Another aspect of the present invention is directed to a manipulator including: a flexible sheath; an end effector disposed at a distal end of the flexible sheath; an actuator disposed at a proximal end of the flexible sheath, the actuator configured to actuate the end effector; a wire configured to transmit power to the end effector, wherein the flexible sheath includes: a flexible inner tube having a lumen along a longitudinal direction thereof, the lumen configured to insert the wire; a flexible outer tube disposed to cover an outer circumferential surface of the inner tube, the outer tube having a higher compression stiffness than the inner tube; and a cushioning disposed at a space between an inner surface of the outer tube and an outer surface of the inner tube, the cushioning is formed by at least one of filling the space with a viscous material and disposing an elastic sheet at the space.

Another aspect of the present invention is a manipulator including: a flexible sheath; an end effector at a distal end of the flexible sheath; an actuator at a proximal end of the flexible sheath, the actuator configured to actuate the end effector; a wire configured to transmit power to the end effector, wherein the flexible sheath includes: a flexible inner tube having a lumen along a longitudinal direction thereof, the lumen configured to insert the wire; a flexible outer tube disposed to cover an outer circumferential surface of the inner tube, the outer tube having a higher compression stiffness than the inner tube; and a protrusion formed on an inner surface of the outer tube, the protrusion being formed of an elastic material protruding in a radial direction of the outer tube.

DESCRIPTION OF EMBODIMENTS

A flexible manipulator sheath 1 according to one embodiment of the present invention will now be described with reference to the drawings.

Figure 1:
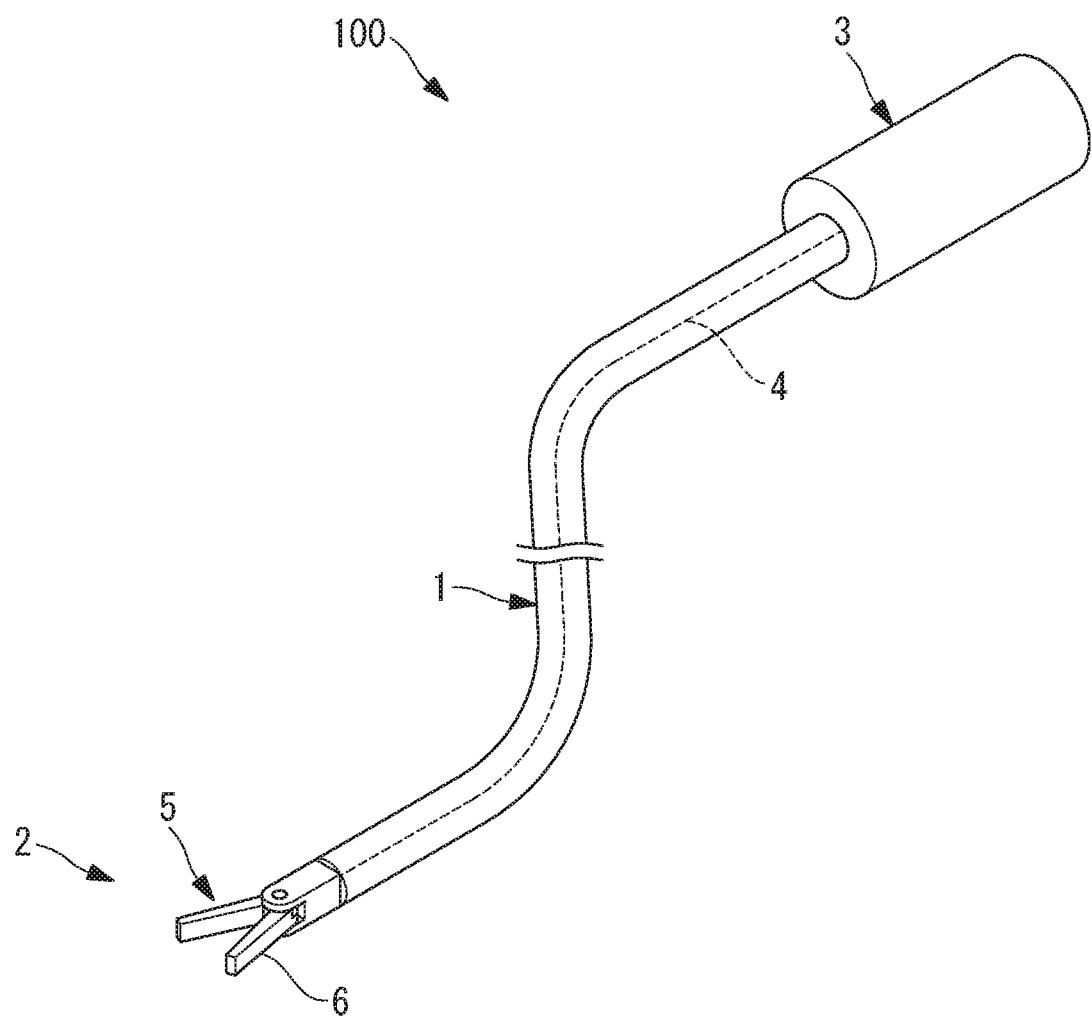
FIG. 1 is a diagram illustrating the overall structure of a flexible manipulator equipped with a flexible-manipulator sheath according to one embodiment of the present invention.

As illustrated in FIG. 1, a flexible manipulator 100 is equipped with: the flexible manipulator sheath 1 of this embodiment; a manipulator 2 disposed at a distal end of the flexible manipulator sheath 1; a drive unit 3 that generates power for actuating the manipulator 2, the drive unit 3 being disposed at a proximal end of the manipulator 2; and a wire 4 that transmits the power generated in the drive unit 3 to the manipulator 2.

The manipulator 2 is equipped with a movable unit 5 having one or more joints, and an end effector 6 supported by a distal end of the movable unit 5.

The drive unit 3 (actuator) is equipped with, for example, a motor (not illustrated) and a pulley 7 that transmits the power from the motor to the wire 4.

Figure 2:
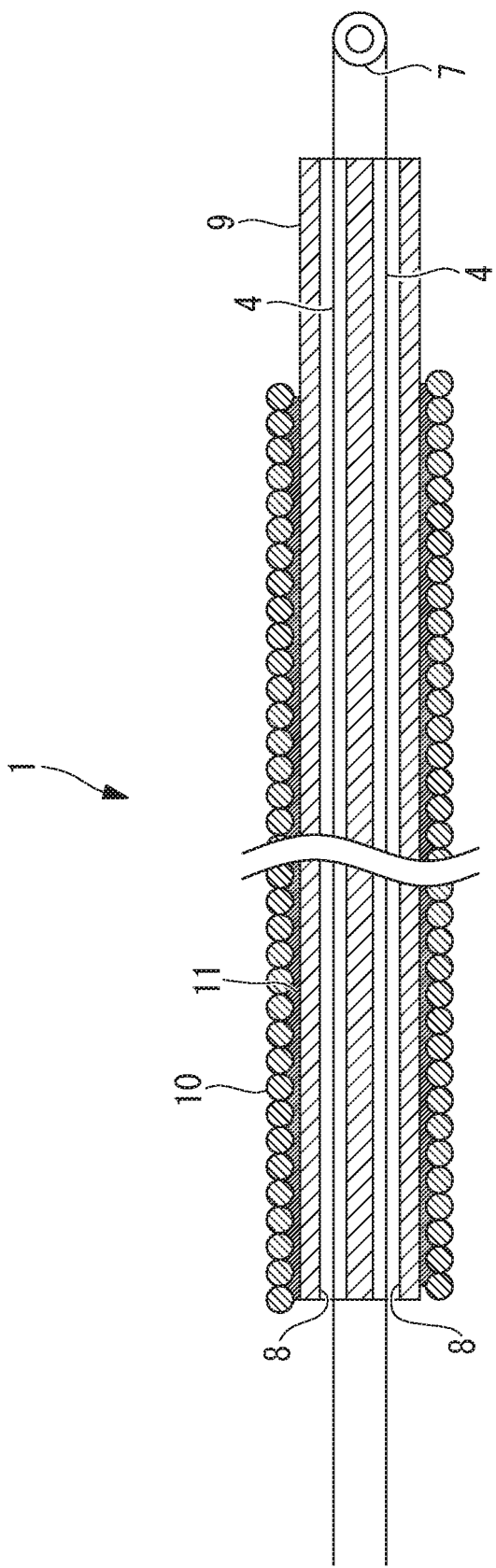
FIG. 2 is a vertical sectional view of the flexible-manipulator sheath illustrated in FIG. 1.

As illustrated in FIG. 2, the flexible manipulator sheath 1 of this embodiment is equipped with a resin multi-lumen tube (inner tube) 9 having a plurality of lumens 8 penetrating therethrough in the longitudinal direction, and a coil tube (outer tube) 10, inside of which the multi-lumen tube 9 is passed through.

The lumens 8 of the multi-lumen tube 9 allow the wire 4 to pass through. The wire 4 passing through the lumens 8 has two end portions respectively connected to the manipulator 2 at the distal end of the flexible manipulator sheath 1 and the drive unit 3 at the proximal end of the flexible manipulator sheath 1.

In this embodiment, a gap between the multi-lumen tube 9 and the coil tube 10 is filled with a cushioning material 11 formed of a viscous material, such as a silicone oil or a low-hardness silicone rubber.

The effects of the flexible manipulator sheath 1 of this embodiment configured as such will now be described.

With the flexible manipulator sheath 1 of this embodiment, even when a tension applied to the wire 4 by the drive unit 3 generates friction between the wire 4 and the inner surfaces of the lumens 8 and thereby elastically deforms the flexible multi-lumen tube 9, the multi-lumen tube 9 remains supported by the coil tube 10 via the cushioning material 11, which fills the space between the multi-lumen tube 9 and the coil tube 10.

Since the coil tube 10 has a higher compression stiffness than the multi-lumen tube 9, deformation of the multi-lumen tube 9 is suppressed, and changes in the path length of the wire 4 can be prevented. This provides an advantage in that it becomes possible to prevent an issue of having the manipulator 2 driven in an unintended direction, which arises due to a change in path length of one portion of the wire 4 caused by applying a tension to another portion of the wire 4. Furthermore, the movable unit 5 of the manipulator 2 can be controlled with accuracy.

Moreover, although deformation of the multi-lumen tube 9 can be prevented with more certainty if the entire outer circumferential surface of the multi-lumen tube 9 can make close contact with the inner surface of the coil tube 10, excessive friction occurs, and it is difficult to insert the multi-lumen tube 9 into the coil tube 10. According to the flexible manipulator sheath 1 of this embodiment, the gap can be evenly filled by causing a silicone oil or low-hardness silicone rubber, which has flowability, to flow. In the case where the gap is extremely narrow, the multi-lumen tube 9 may be inserted in the inner hole of the coil tube 10 filled with the cushioning material 11 while pushing out the cushioning material 11 filling the inner hole.

Figure 3:
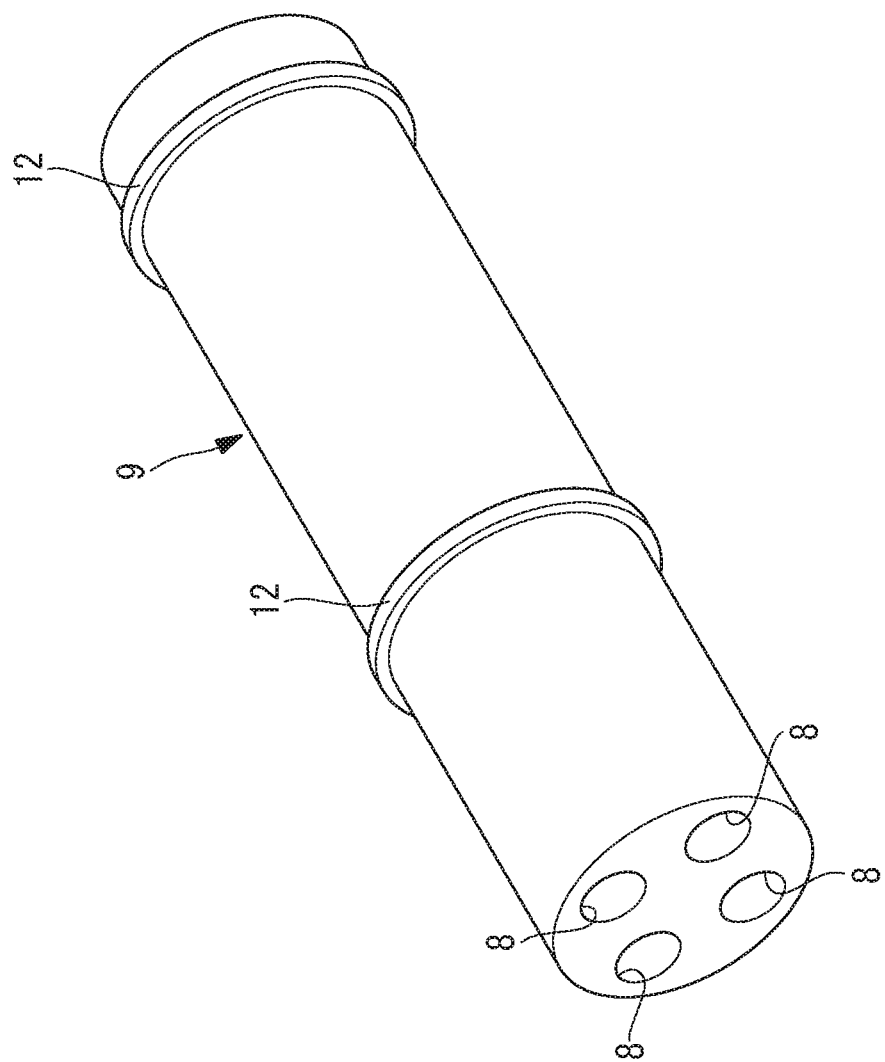
FIG. 3 is a perspective view of an inner tube according to a modification of the flexible-manipulator sheath illustrated in FIG. 1.

In this embodiment, as illustrated in FIG. 3, a plurality of annular protrusions (cushioning-material retaining portions or partitioning wall portions) 12 may be disposed on the outer surface of the multi-lumen tube 9. The annular protrusions 12 each extend all around the circumference and are spaced from one another in the longitudinal direction. Alternatively, similar protrusions that protrude radially inward may be formed on the inner surface of the coil tube 10.

In this manner, when the multi-lumen tube 9 is inserted into the inner hole of the coil tube 10, the protrusions 12 divide the gap between the multi-lumen tube 9 and the coil tube 10 into a plurality of sections in the longitudinal direction. As a result, the cushioning material 11, which has flowability, is prevented from flowing in the longitudinal direction during insertion of the multi-lumen tube 9 into the coil tube 10, and thus can be retained between the protrusions 12.

Figure 4:
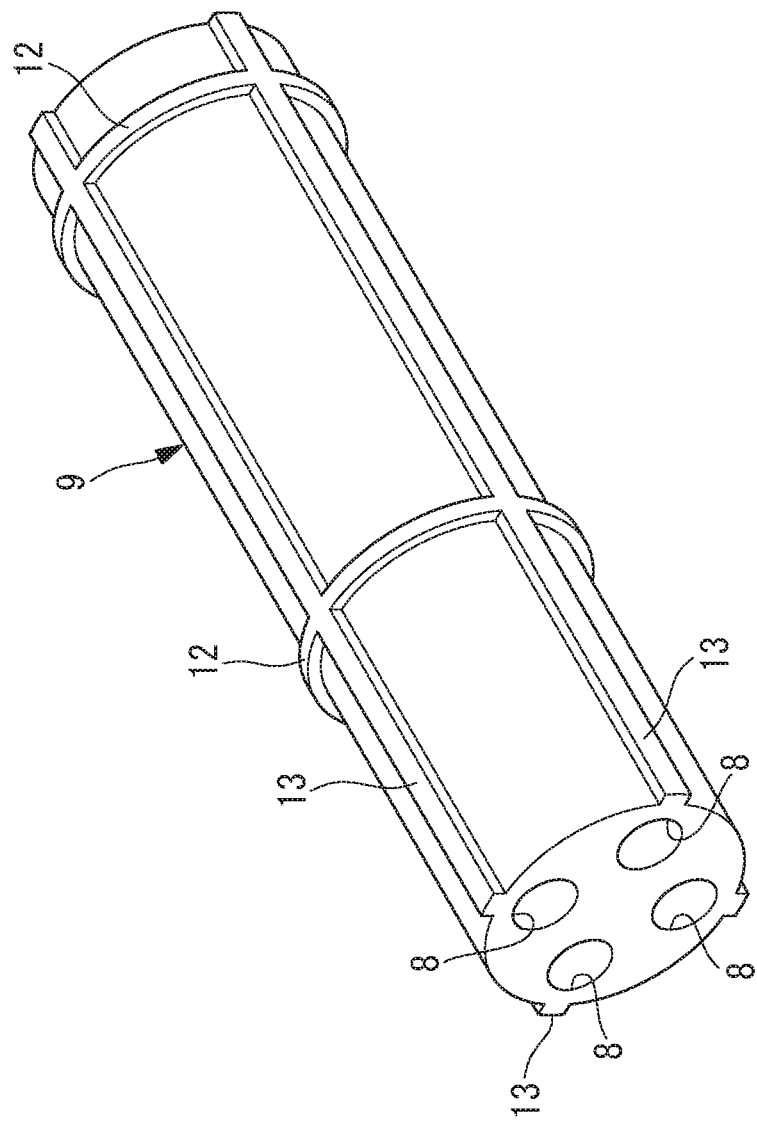
FIG. 4 is a perspective view of an inner tube according to another modification of the flexible-manipulator sheath illustrated in FIG. 1.

Furthermore, as illustrated in FIG. 4, protrusions (cushioning-material retaining portions) 13 for subdividing the sections in the circumferential direction may be additionally formed. By doing so, it becomes possible to prevent the cushioning material 11 from being pushed out in the circumferential direction from a radially thin portion of the tubular gap between the multi-lumen tube 9 and the coil tube 10.

The cushioning-material retaining portions may take the form of a mesh member, which has large openings, wound around the outer surface of the multi-lumen tube 9 so that the tubular gap can be divided into sections in the same manner as with the protrusions 12 and 13.

Figure 5:
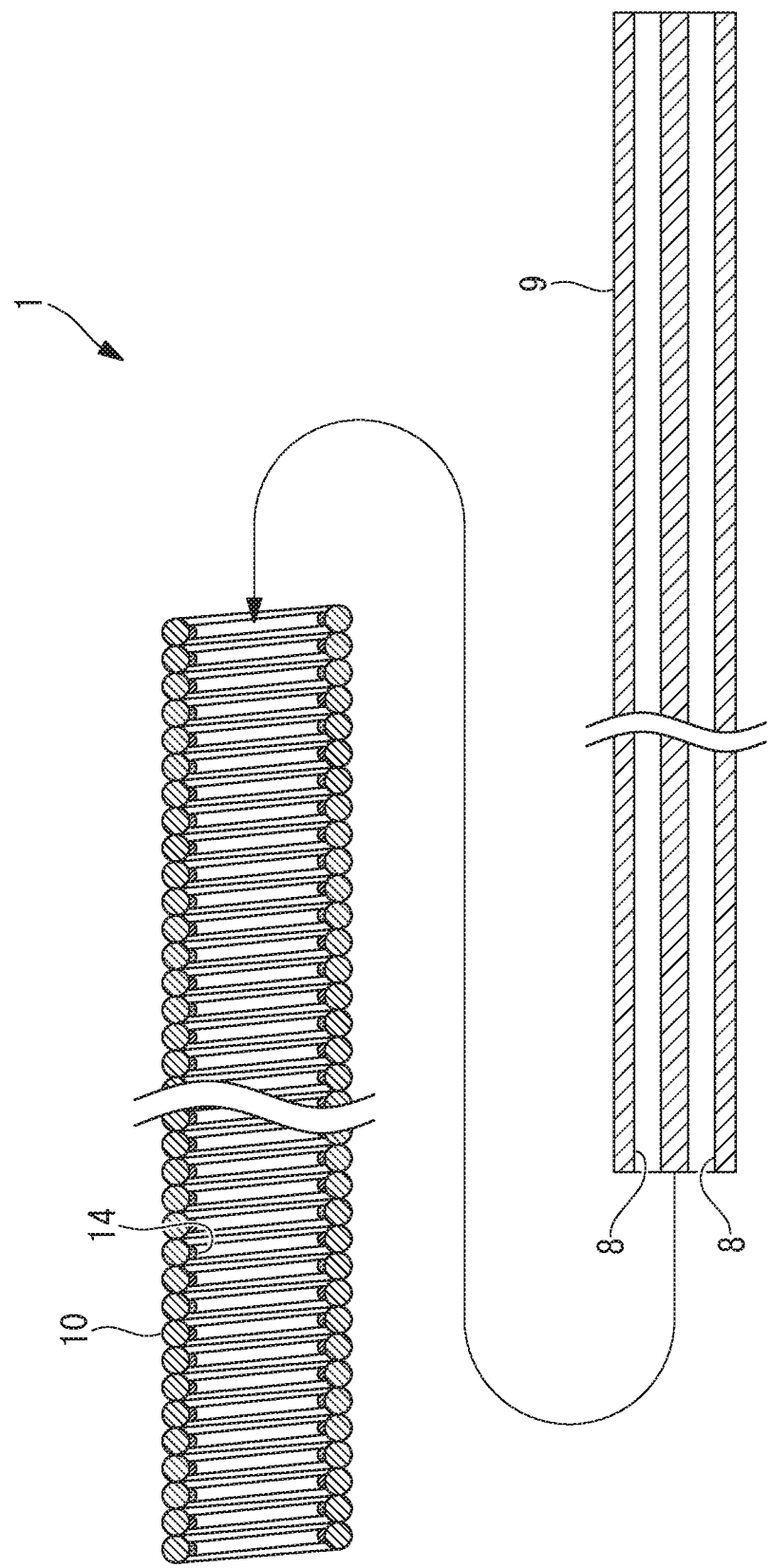
FIG. 5 is a vertical sectional view of another modification of the flexible-manipulator sheath illustrated in FIG. 1.

In this embodiment, the cushioning material 11 having flowability fills the gap. Alternatively, as illustrated in FIG. 5, protrusions 14 formed of an elastic material may be provided on the inner surface of the coil tube 10 so as to serve as the cushioning material. In this manner, when the multi-lumen tube 9 is inserted into the inner hole of the coil tube 10, the protrusions 14 are elastically deformed, and the tips of the protrusions 14 come into close contact with the outer surface of the multi-lumen tube 9. Thus, the multi-lumen tube 9 is supported by the coil tube 10 via the cushioning material formed of the protrusions 14.

In the example illustrated in FIG. 5, the protrusions 14 are continuously formed throughout the entire length on the radially inner-side surface of the wire material constituting the coil tube 10; however, the protrusions 14 may be formed intermittently. When the coil tube 10 is formed of a plurality of coils, the protrusions 14 may be formed on the inner surface of some of the coils so as to reduce the number of protrusions 14.

The protrusions 14 preferably have, as a surface on the radially inner side, a convex curved surface protruding radially inward. By doing so, it becomes possible to reduce the contact area between the multi-lumen tube 9 and the protrusions 14 and to improve the ease of inserting the multi-lumen tube 9 into the coil tube 10.

In this embodiment, a multi-lumen tube 9 having four lumens 8 is described as an example of the inner tube. Alternatively, a single lumen tube that has one lumen 8 or a multi-lumen tube having any number of lumens 8 greater than 1 may be employed.

In this embodiment, a multi-lumen tube 9 in which the lumens 8 extend straight along the longitudinal direction is described as an example. Alternatively, a twisted multi-lumen tube 9 in which lumens 8 are twisted in one direction about the center axis may be employed.

The outer tube may be any desired tube instead of the coil tube 10.

Figure 6:
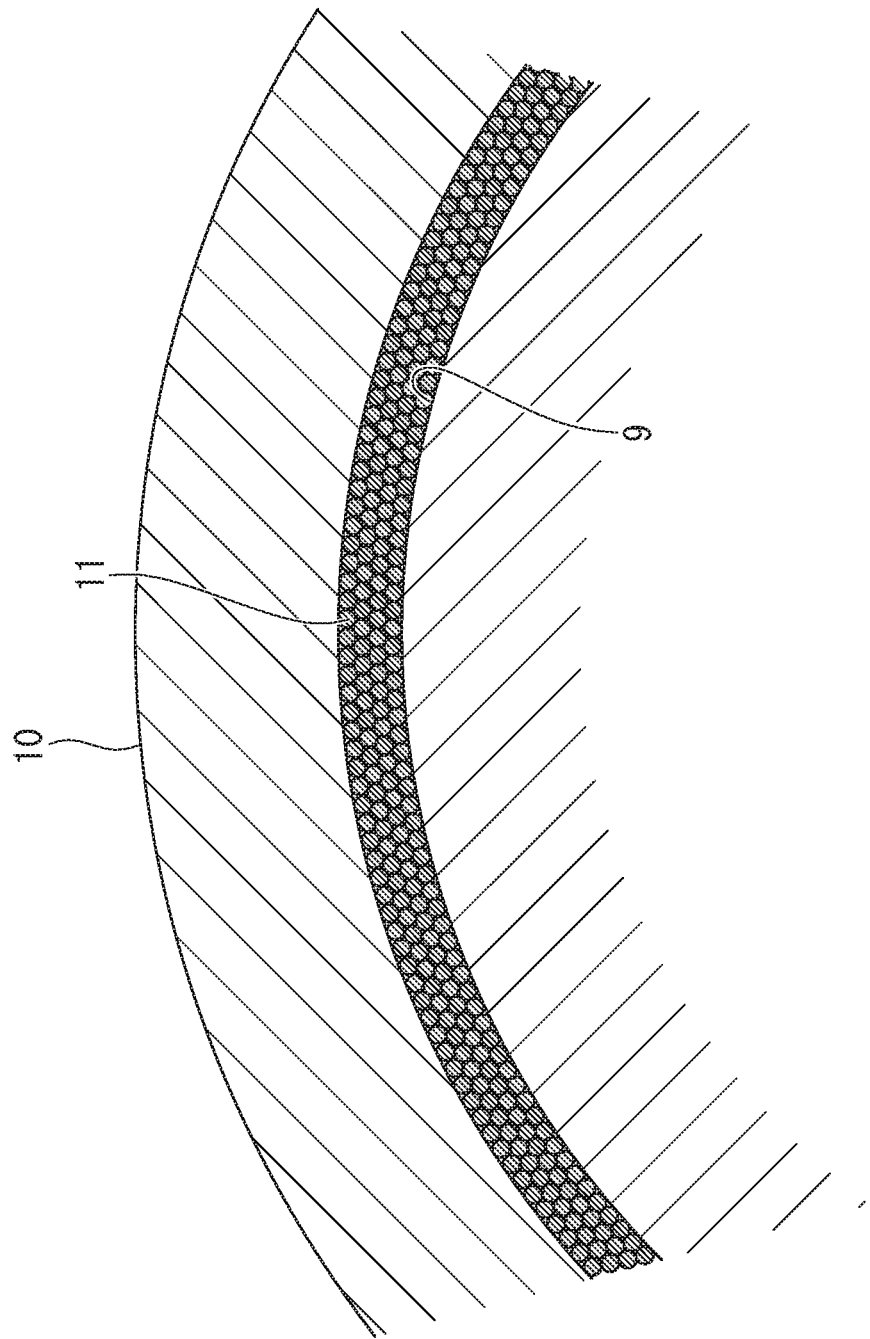
FIG. 6 is a partial horizontal sectional view of another modification of the flexible-manipulator sheath illustrated in FIG. 1.

As illustrated in FIG. 6, a fiber material, such as glass fibers, that extends in the longitudinal direction in the gap between the coil tube 10 and the multi-lumen tube 9 and fills the gap by being aligned in the circumferential direction and the radial direction may be employed as the cushioning material 11.

In this manner, while the flexibility of the flexible manipulator sheath 1 is maintained, the multi-lumen tube 9 can be securely supported by the coil tube 10 via the cushioning material 11, and the ease of inserting the multi-lumen tube 9 into the coil tube 10 can be improved by allowing the fibers to slide relative to one another.

Alternatively, a sheet material (not illustrated) composed of an elastic material disposed all around the circumference in the gap between the multi-lumen tube 9 and the coil tube 10 may be provided as the cushioning material 11. The sheet material may be continuous throughout the entire length or may be intermittent.

As a result, the above-described embodiment also leads to the following aspect.

One aspect of the present invention provides a flexible-manipulator sheath, the sheath including a flexible inner tube equipped with a lumen through which a wire is passed along a longitudinal direction; a flexible outer tube disposed to cover an outer circumferential surface of the inner tube, the outer tube having a higher compression stiffness than the inner tube; and a cushioning material interposed between the outer tube and the inner tube so that deformation of an outer surface of the inner tube is supported by an inner surface of the outer tube.

According to this aspect, when a tension is applied to a proximal end of a wire passed through the lumen to drive a manipulator movable unit at the distal end, friction between the wire and the inner surface of the lumen causes the flexible inner tube to deform; however, since deformation of the inner tube is supported by the outer tube via the cushioning material in the gap between the inner tube and the outer tube, deformation is avoided. As a result, even when the wire is pulled, changes in the path length of the wire are suppressed, and the manipulator can be controlled with accuracy.

In the aspect described above, the cushioning material may be a viscous material filling a space between the outer tube and the inner tube.

In this manner, even when pulling the wire causes the inner tube to deform, the cushioning material formed of a viscous material filling the space between the outer tube and the inner tube suppresses deformation. Thus, changes in wire path lengths are suppressed, and the manipulator can be controlled with accuracy.

In the aspect described above, the cushioning material may be formed of a silicone oil or a low-hardness silicone rubber.

In this manner, the space between the inner tube and the outer tube can be easily filled with the silicone oil or low-hardness silicone rubber, which has flowability. Since the silicone oil or the low-hardness silicone rubber has high viscosity, deformation of the inner tube can be suppressed.

In the aspect described above, the flexible-manipulator sheath may further include a cushioning-material retaining portion that retains the cushioning material in the space between the outer tube and the inner tube.

In this manner, although the flowable cushioning material, such as the silicone oil and the low-hardness silicone rubber, may flow as the gap widens, the cushioning-material retaining portion retains the cushioning material within the space between the outer tube and the inner tube, and thus the effect of preventing deformation of the inner tube can be maintained.

In the aspect described above, the cushioning-material retaining portion may be a partitioning wall portion disposed on the inner surface of the outer tube or the outer surface of the inner tube so as to divide the space in the longitudinal direction.

In this manner, the cushioning material is retained in the spaces divided by the partitioning wall portion, and the effect of preventing deformation of the inner tube can be maintained.

In the aspect described above, the cushioning material may be a plurality of fiber materials that extend in the longitudinal direction and are aligned in a circumferential direction and a radial direction.

In this manner, because the space is filled with fibers, flexibility is maintained while deformation of the inner tube is prevented.

The present invention provides advantageous effects in that changes in wire path length are suppressed and a manipulator can be controlled with accuracy even when the tension applied to a wire passed through a lumen is increased.

REFERENCE SIGNS LIST 1 flexible manipulator sheath
4 wire
8 lumen
9 multi-lumen tube (inner tube)
10 coil tube (outer tube)
11 cushioning
12, 13, 14 protrusions (cushioning-material retaining portion, partitioning wall portion, cushioning material)

The invention claimed is:

1. A flexible-manipulator sheath comprising:
a flexible inner tube having a lumen along a longitudinal direction thereof, the lumen configured to insert a wire;
a flexible outer tube disposed to cover an outer circumferential surface of the inner tube, the outer tube having a higher compression stiffness than the inner tube; and
a cushioning disposed at a space between an inner surface of the outer tube and an outer surface of the inner tube,
wherein the cushioning is formed by at least one of filling the space with a viscous material and disposing an elastic sheet at the space.

2. The flexible-manipulator sheath according to claim 1, wherein the cushioning is formed of a silicone oil or a low-hardness silicone rubber.

3. The flexible-manipulator sheath according to claim 1, further comprising a cushioning retaining portion configured to secure the space and retain the cushioning.

4. The flexible-manipulator sheath according to claim 3, wherein the cushioning retaining portion comprises a protrusion disposed on the inner surface of the outer tube or the outer surface of the inner tube.

5. The flexible-manipulator sheath according to claim 4, wherein the protrusion comprises a plurality of protrusions.

6. The flexible-manipulator sheath according to claim 4, wherein the protrusion has a ring shape and extends all around a circumference on the outer surface of the inner tube.

7. The flexible-manipulator sheath according to claim 4, wherein the protrusion extends in a longitudinal direction on the outer surface of the inner tube.

8. A manipulator comprising:
a flexible sheath;
an end effector disposed at a distal end of the flexible sheath;
an actuator disposed at a proximal end of the flexible sheath, the actuator configured to actuate the end effector;
a wire configured to transmit power to the end effector,
wherein the flexible sheath comprises:
a flexible inner tube having a lumen along a longitudinal direction thereof, the lumen configured to insert the wire;
a flexible outer tube disposed to cover an outer circumferential surface of the inner tube, the outer tube having a higher compression stiffness than the inner tube; and
a cushioning disposed at a space between an inner surface of the outer tube and an outer surface of the inner tube, the cushioning is formed by at least one of filling the space with a viscous material and disposing an elastic sheet at the space.

9. The manipulator according to claim 8, wherein the cushioning is formed of a silicone oil or a low-hardness silicone rubber.

10. The manipulator according to claim 8, further comprising a cushioning retaining portion configured to secure the space and retain the cushioning.

11. The manipulator according to claim 10, wherein the cushioning retaining portion comprises a protrusion disposed on the inner surface of the outer tube or the outer surface of the inner tube.

12. A manipulator comprising:
a flexible sheath;
an end effector at a distal end of the flexible sheath;
an actuator at a proximal end of the flexible sheath, the actuator configured to actuate the end effector;

a wire configured to transmit power to the end effector,
wherein the flexible sheath comprises:
- a flexible inner tube having a lumen along a longitudinal direction thereof, the lumen configured to insert the wire;
- a flexible outer tube disposed to cover an outer circumferential surface of the inner tube, the outer tube having a higher compression stiffness than the inner tube; and
- a protrusion formed on an inner surface of the outer tube, the protrusion being formed of an elastic material protruding in a radial direction of the outer tube.

13. The manipulator according to claim 12, wherein the protrusion comprises a plurality of protrusions.

14. The manipulator according to claim 12, wherein the protrusion has a ring shape and extends all around a circumference on the inner surface of the outer tube.

15. The manipulator according to claim 12, wherein the protrusion has a convex curved surface.

* * * * *